United States Patent
Kolesa et al.

(10) Patent No.: US 11,420,945 B2
(45) Date of Patent: Aug. 23, 2022

(54) SOLID STATE FORMS OF PEMAFIBRATE

(71) Applicant: TEVA PHARMACEUTICALS INTERNATIONAL GMBH, Jona (CH)

(72) Inventors: Pavel Kolesa, Haj Ve Slezsku (CZ); Andrea Colombo, Parabiago (IT); Ettore Marzorati, Corsico (IT)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 50 days.

(21) Appl. No.: 16/957,179

(22) PCT Filed: Dec. 21, 2018

(86) PCT No.: PCT/US2018/067012
§ 371 (c)(1),
(2) Date: Jun. 23, 2020

(87) PCT Pub. No.: WO2019/133462
PCT Pub. Date: Jul. 4, 2017

(65) Prior Publication Data
US 2021/0380543 A1    Dec. 9, 2021

Related U.S. Application Data

(60) Provisional application No. 62/645,300, filed on Mar. 20, 2018, provisional application No. 62/631,119, filed on Feb. 15, 2018, provisional application No. 62/623,227, filed on Jan. 29, 2018, provisional application No. 62/615,074, filed on Jan. 9, 2018, provisional application No. 62/610,651, filed on Dec. 27, 2017.

(51) Int. Cl.
C07D 263/58 (2006.01)

(52) U.S. Cl.
CPC ........ C07D 263/58 (2013.01); *C07B 2200/13* (2013.01)

(58) Field of Classification Search
CPC .......................... C07D 263/58; C07B 2200/13
USPC ....................................................... 548/222
See application file for complete search history.

(56) References Cited

U.S. PATENT DOCUMENTS 6,627,646 B2 * 9/2003 Bakale ............... A61P 37/08
514/322
7,109,226 B2    9/2006 Yamazaki et al.

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.,"J of Pharm. (Lahore), 1979, 1(1), 59-66.*
U.S. Pharmacopia #23, National Formulary#18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
Guillory (in Brittain ed.), polymorphism in Pharmaceutical Solids, NY: Marcel Dekker., 1-2, 183-226. (Year: 1999).*
Rodriguez-Spong et al., "General principles, etc.," Adv. Drug Delivery REviews 56 241-274. (Year: 2004).*
Yamazaki yet Al: "A practical synthesis of the PPARαagonist, (R)-K-13675, starting from (S)-2-hydroxybutyrolactone", Tetrahedron, Elsevier Science Publishers, Amsterdam, NL, vol. 64, No. 35 , Aug. 25, 2008, pp. 8155-8158 (4 pages).
International Search Report and Written Opinion of the International Searching Authority issued in corresponding Int'l Appl. No. PCT/2018/067012 dated Feb. 27, 2019 (12 pages).

* cited by examiner

*Primary Examiner* — Niloofar Rahmani
(74) *Attorney, Agent, or Firm* — Carter, Deluca & Farrell LLP

(57) ABSTRACT

The present disclosure relates to solid state forms of Pemafibrate processes for preparation thereof and pharmaceutical compositions thereof.

5 Claims, 14 Drawing Sheets

Figure 1: An X-ray powder diffractogram (XRPD) of Form A of Pemafibrate
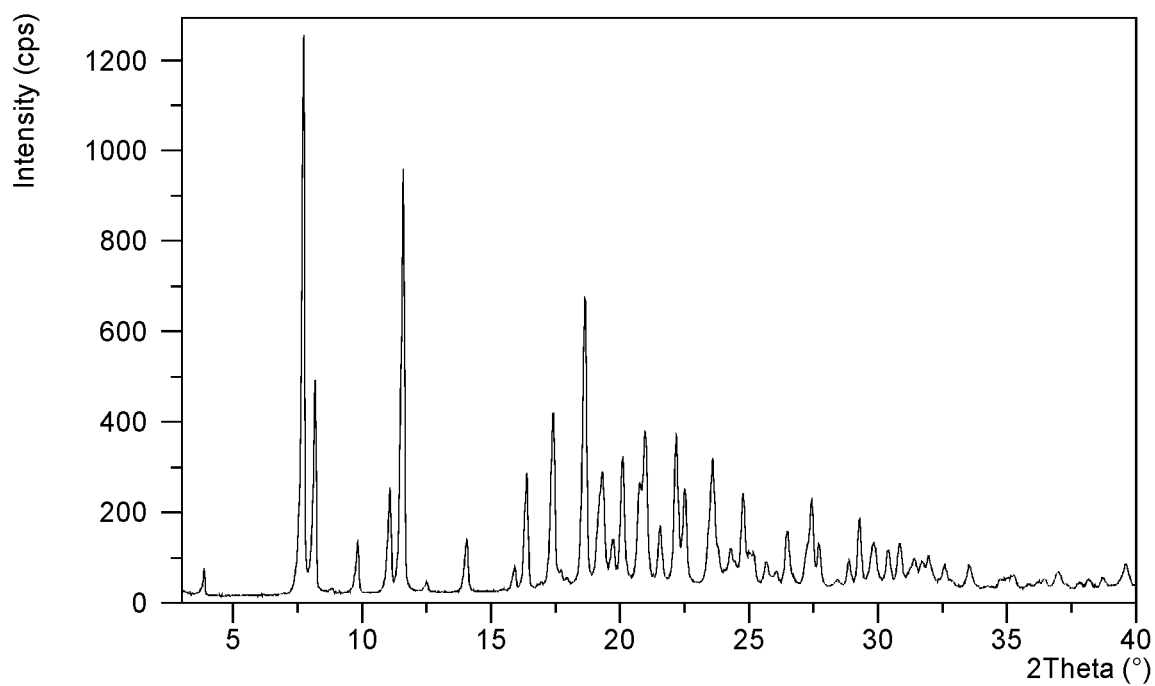

Figure 2: An X-ray powder diffractogram (XRPD) of Form B of Pemafibrate
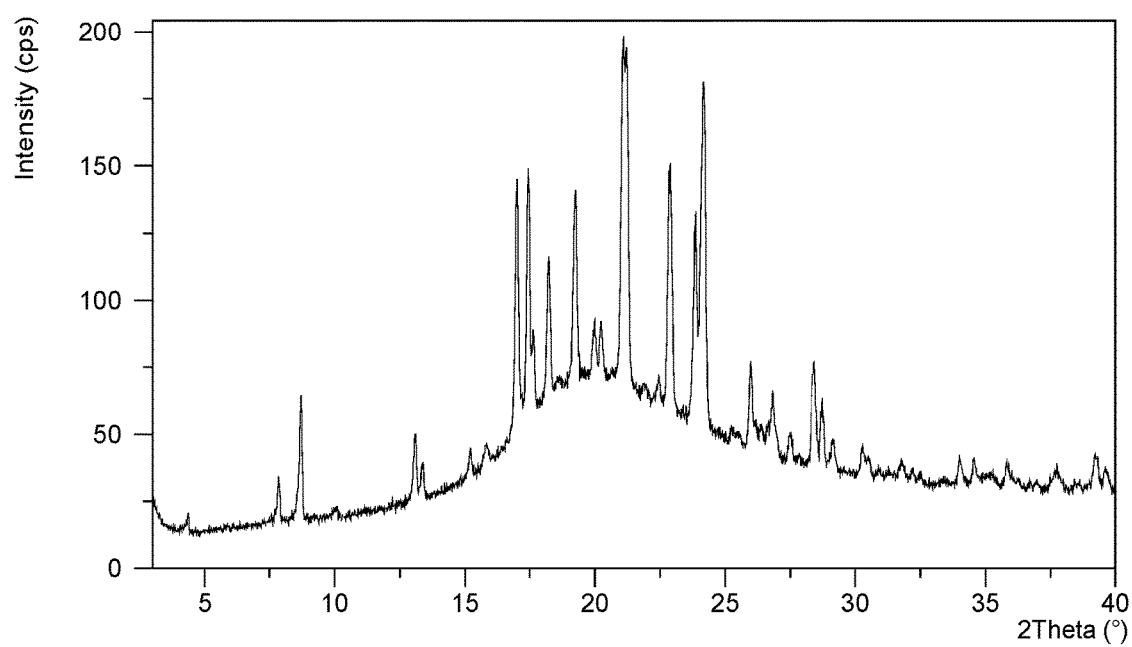

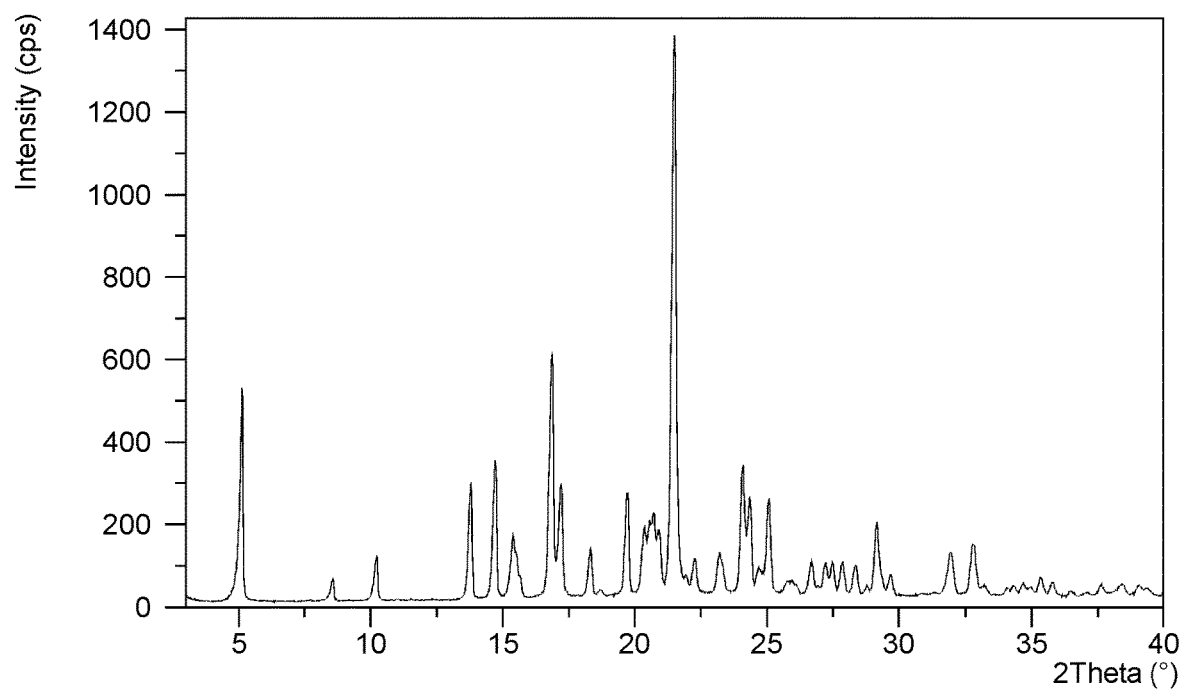
Figure 3: An X-ray powder diffractogram (XRPD) of Form C of Pemafibrate Figure 4: An X-ray powder diffractogram (XRPD) of Form D of Pemafibrate
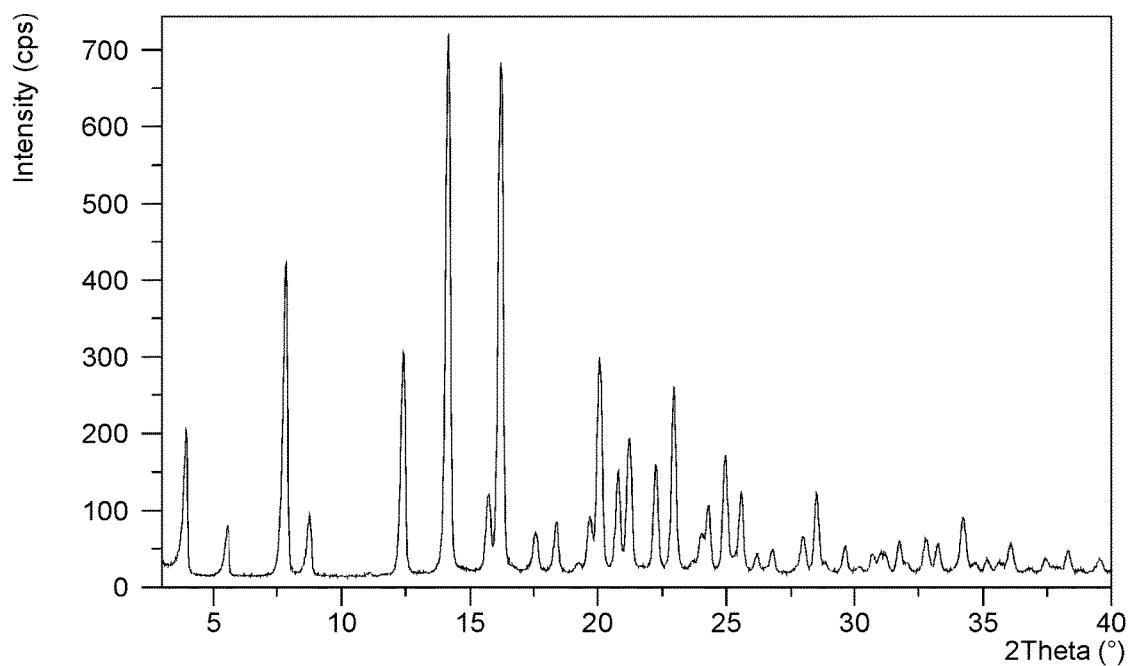

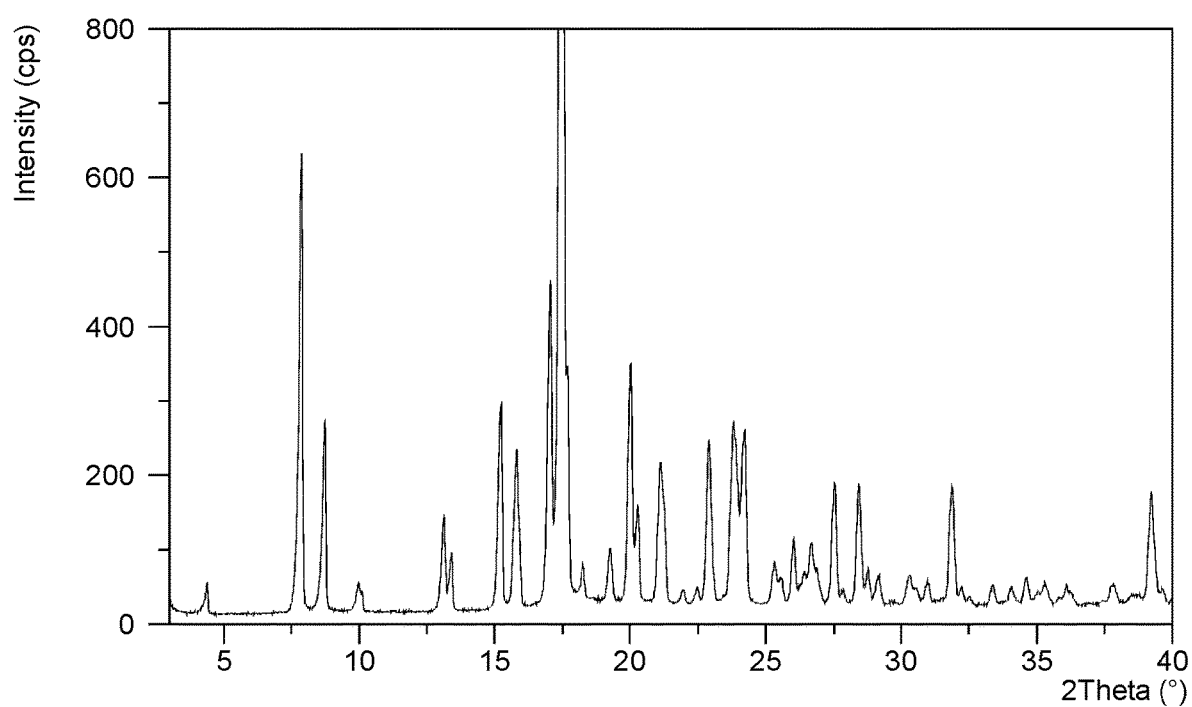
Figure 5: An X-ray powder diffractogram (XRPD) of Form B of Pemafibrate

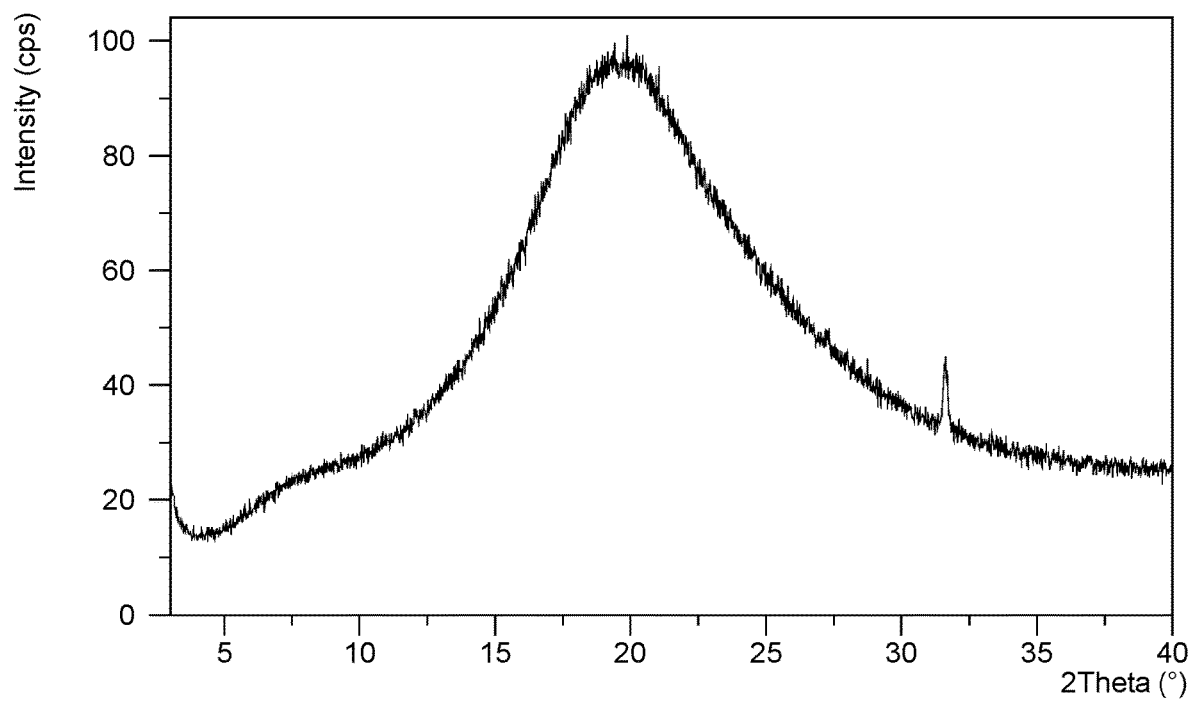
Figure 6: An X-ray powder diffractogram (XRPD) of amorphous form of Pemafibrate Figure 7: A solid state $^{13}$C-NMR spectrum of Form A of Pemafibrate (Figure 7a: 200-0 ppm; Figure 7b: 200-100 ppm; Figure 7c: 100-0 ppm)
Fig 7a: $^{13}$C solid state NMR spectrum (range from 200-0 ppm):
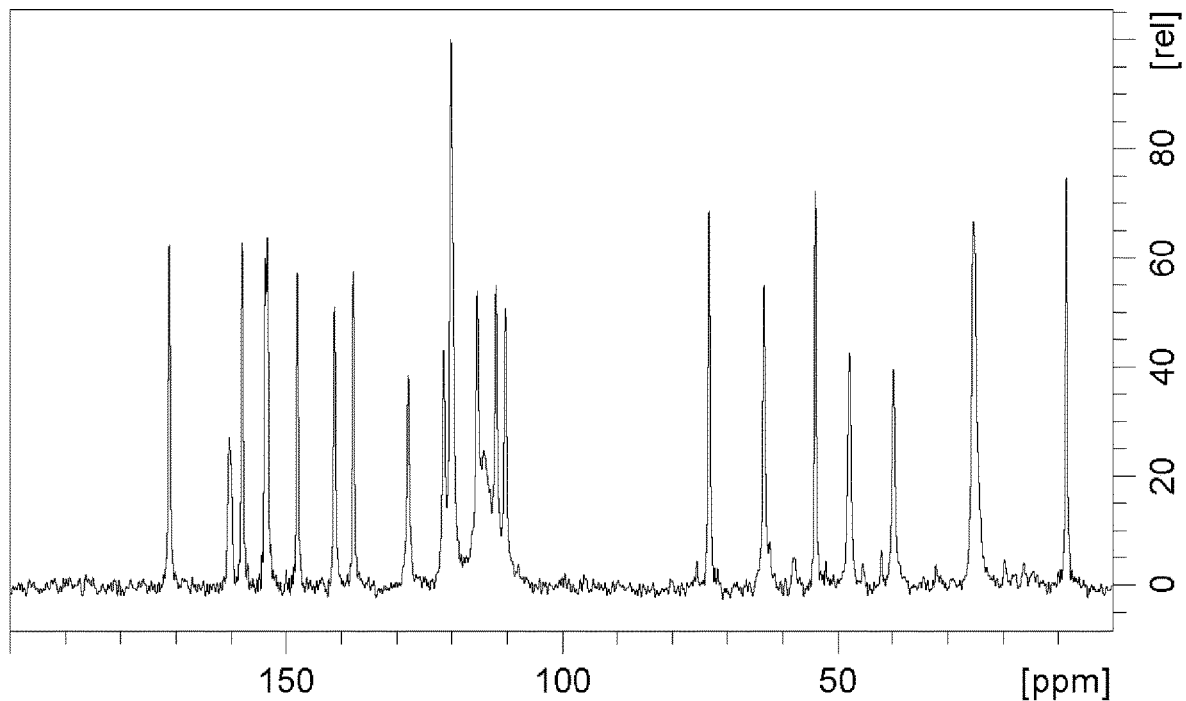
Fig 7b: $^{13}$C solid state NMR spectrum (range from 200-100 ppm):
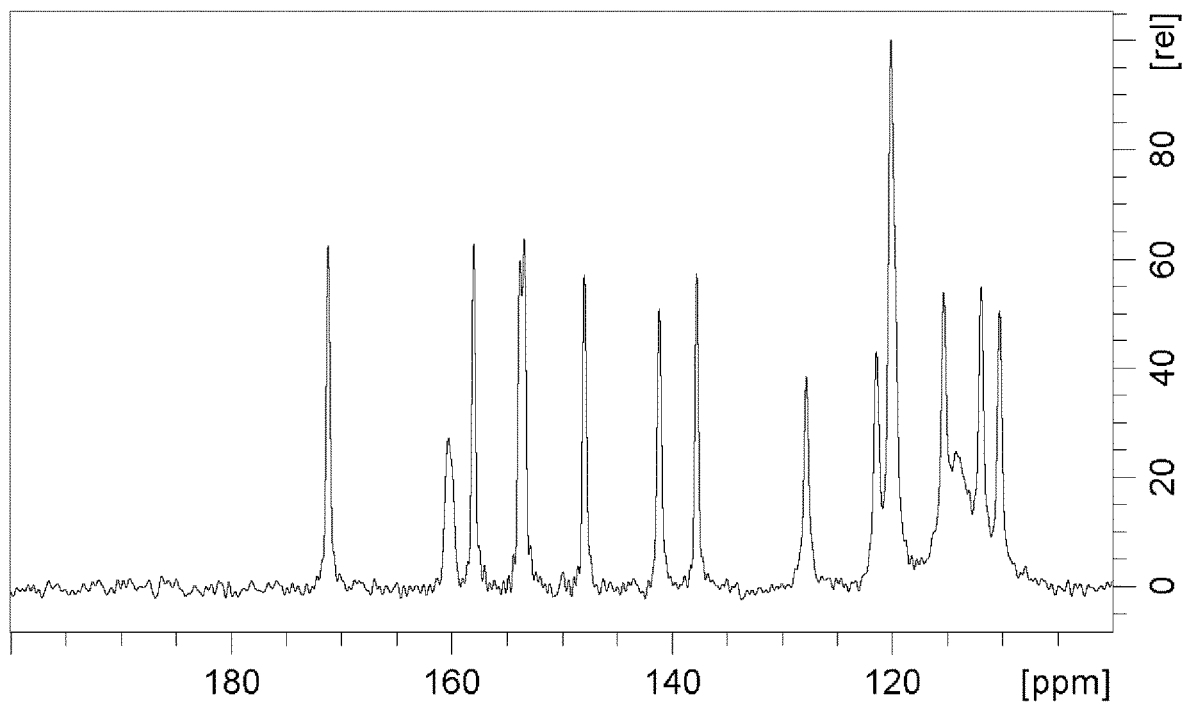

Fig. 7c: $^{13}$C solid state NMR spectrum (range from 100-0 ppm):
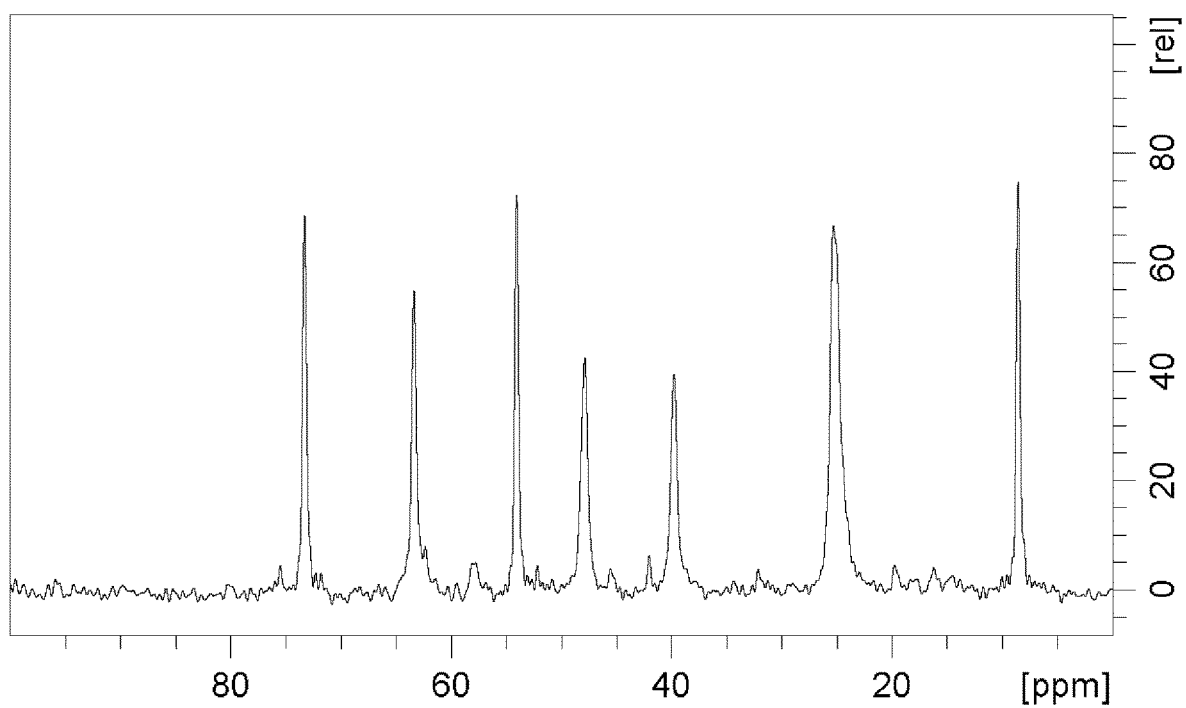

Figure 8: A solid state $^{13}$C-NMR spectrum of Form B of Pemafibrate (Figure 8a: 200-0 ppm; Figure 8b: 200-100 ppm; Figure 8c: 100-0 ppm)
Fig. 8a: $^{13}$C solid state NMR spectrum (range from 200-0 ppm):
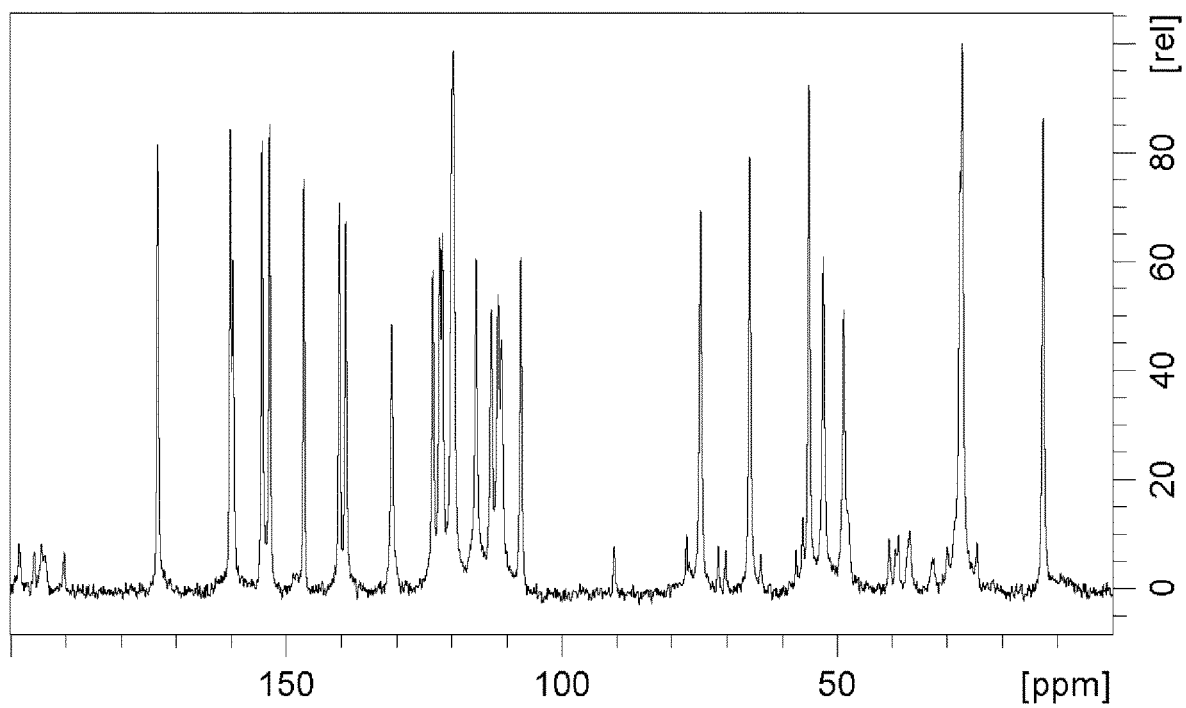

Fig. 8b: $^{13}$C solid state NMR spectrum (range from 200-100 ppm):
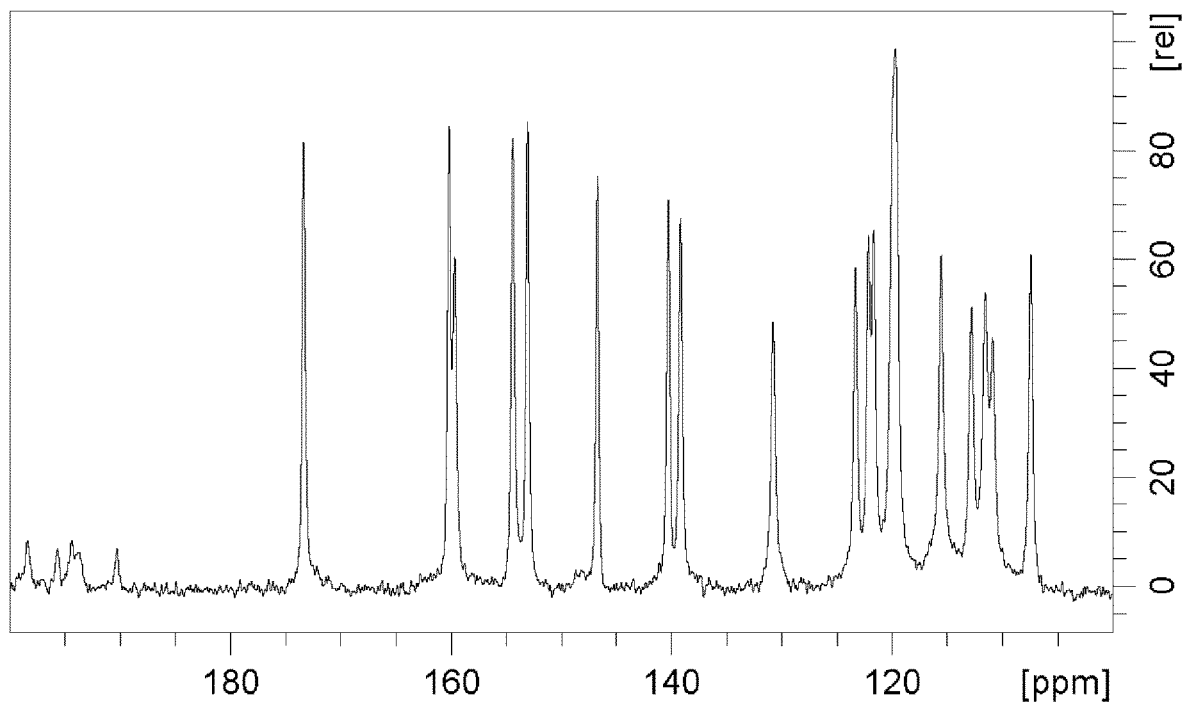
Fig. 8c: $^{13}$C solid state NMR spectrum (range from 100-0 ppm):
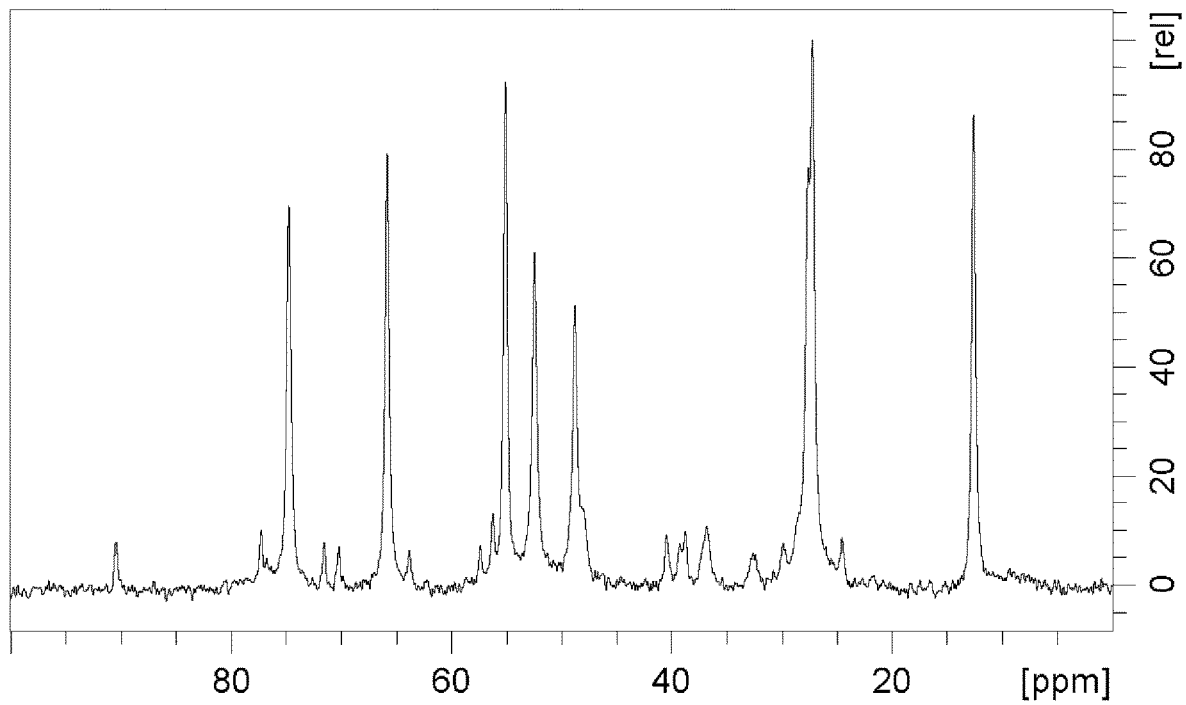

Figure 9: A solid state $^{13}$C-NMR spectrum of Form C of Pemafibrate (Figure 9a: 200-0 ppm; Figure 9b: 200-100 ppm; Figure 9c: 100-0 ppm)
Fig. 9a: $^{13}$C solid state NMR spectrum (range from 200-0 ppm):
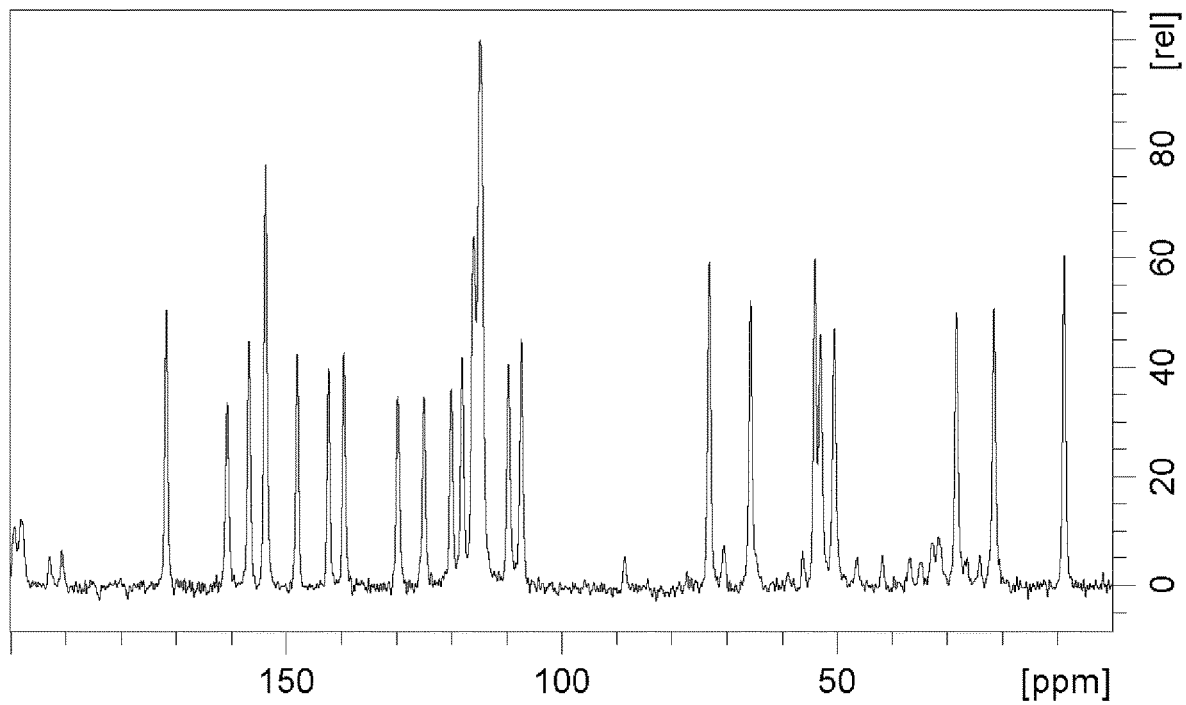
Fig. 9b: $^{13}$C solid state NMR spectrum (range from 200-100 ppm):
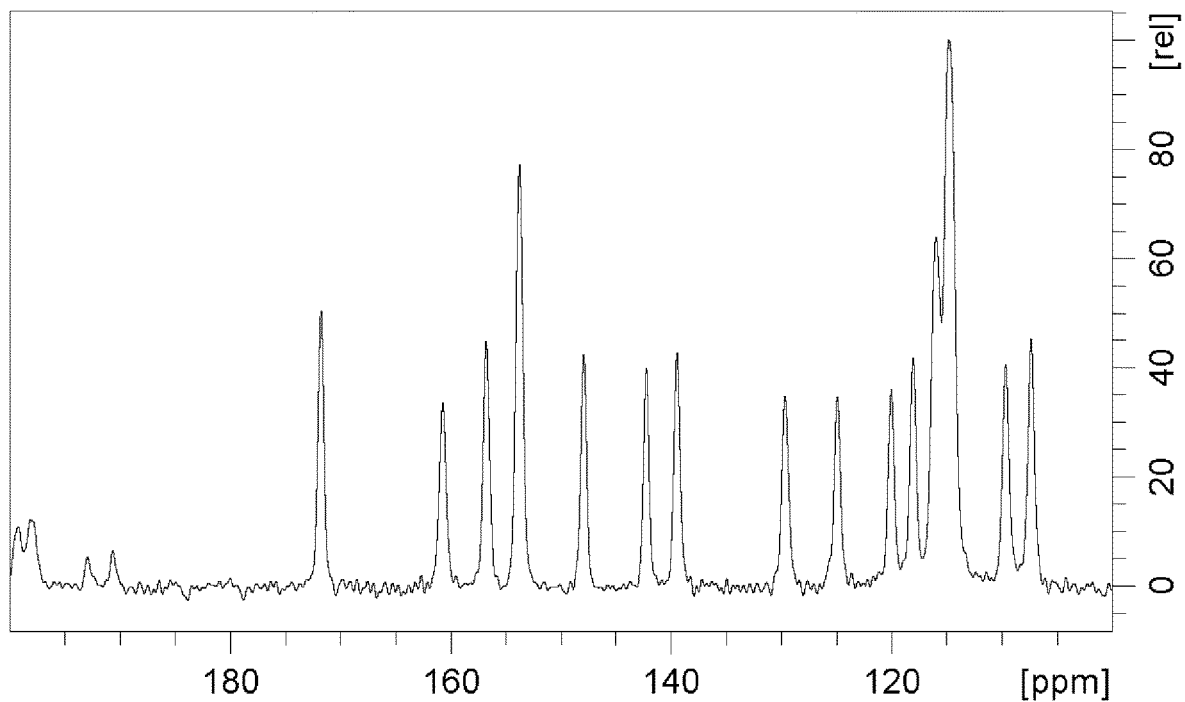

Fig. 9c: $^{13}$C solid state NMR spectrum (range from 100-0 ppm):
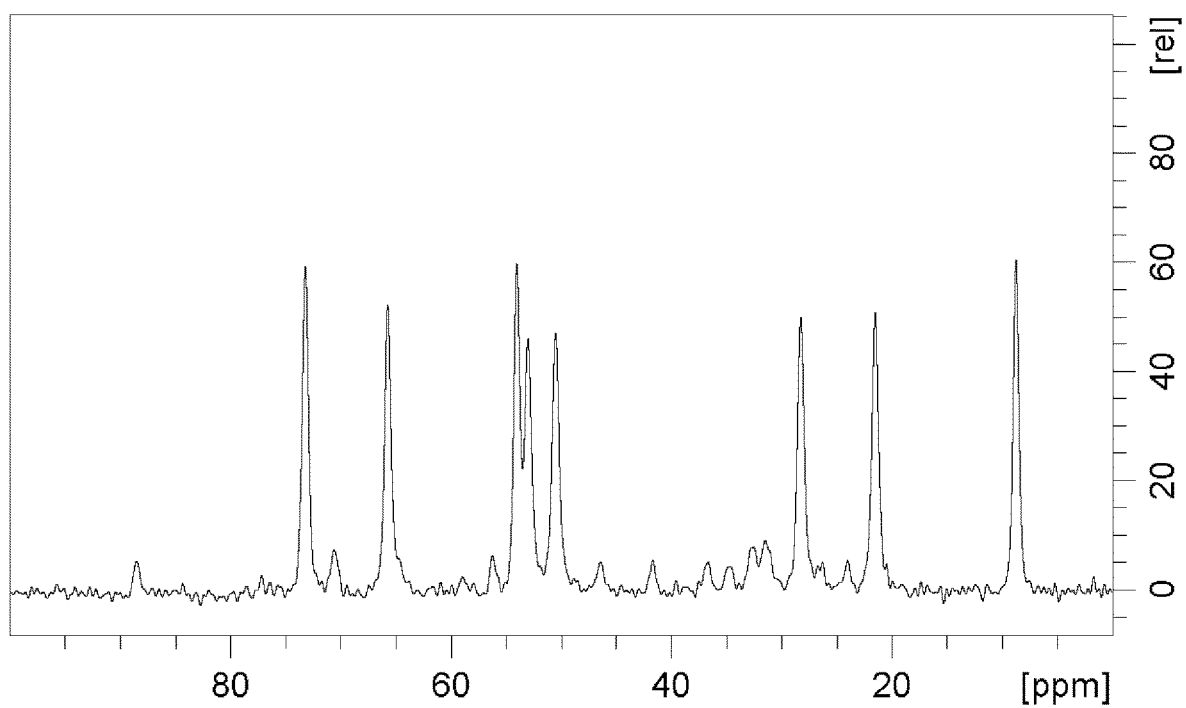

Figure 10: A solid state $^{13}$C-NMR spectrum of Form D of Pemafibrate (Figure 10a: 200-0 ppm; Figure 10b: 200-100 ppm; Figure 10c: 100-0 ppm)
Fig. 10a: $^{13}$C solid state NMR spectrum (range from 200-0 ppm):
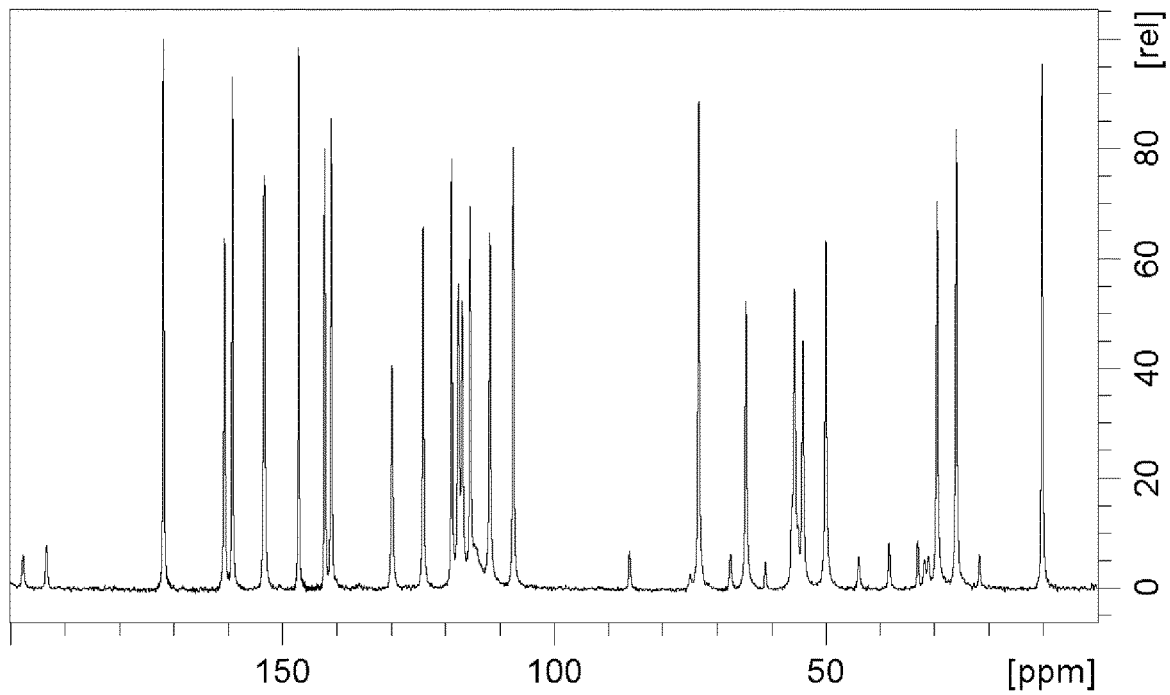
Fig 10b: $^{13}$C solid state NMR spectrum (range from 200-100 ppm):
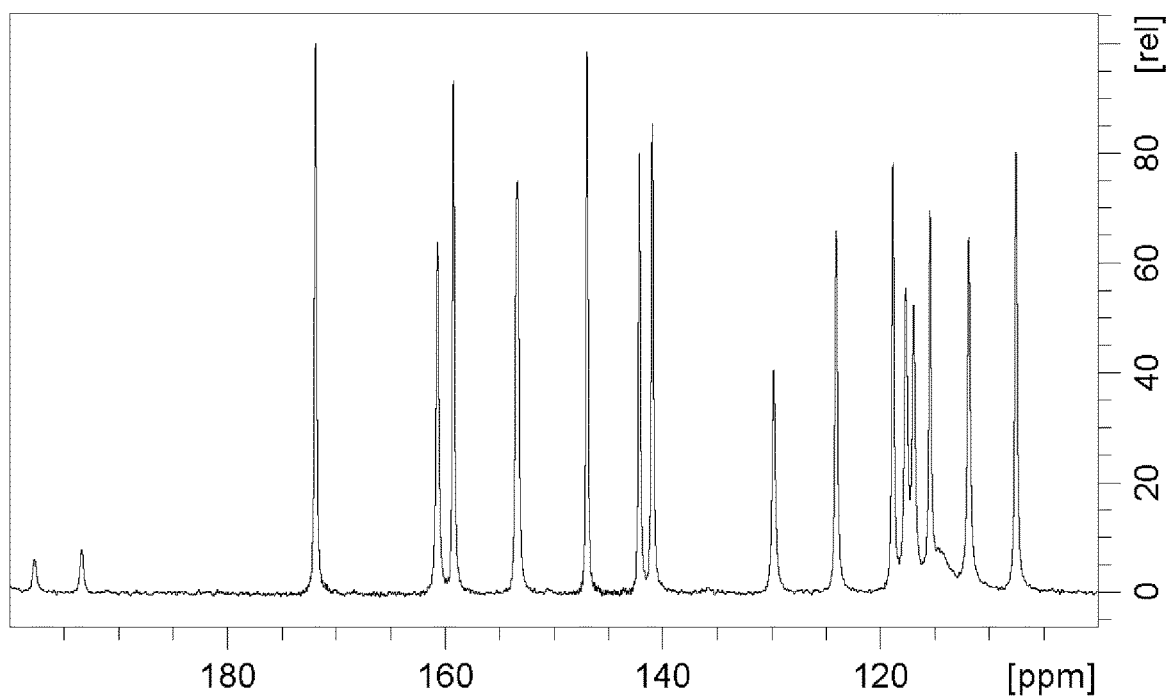

Fig. 10c: $^{13}$C solid state NMR spectrum (range from 100-0 ppm):
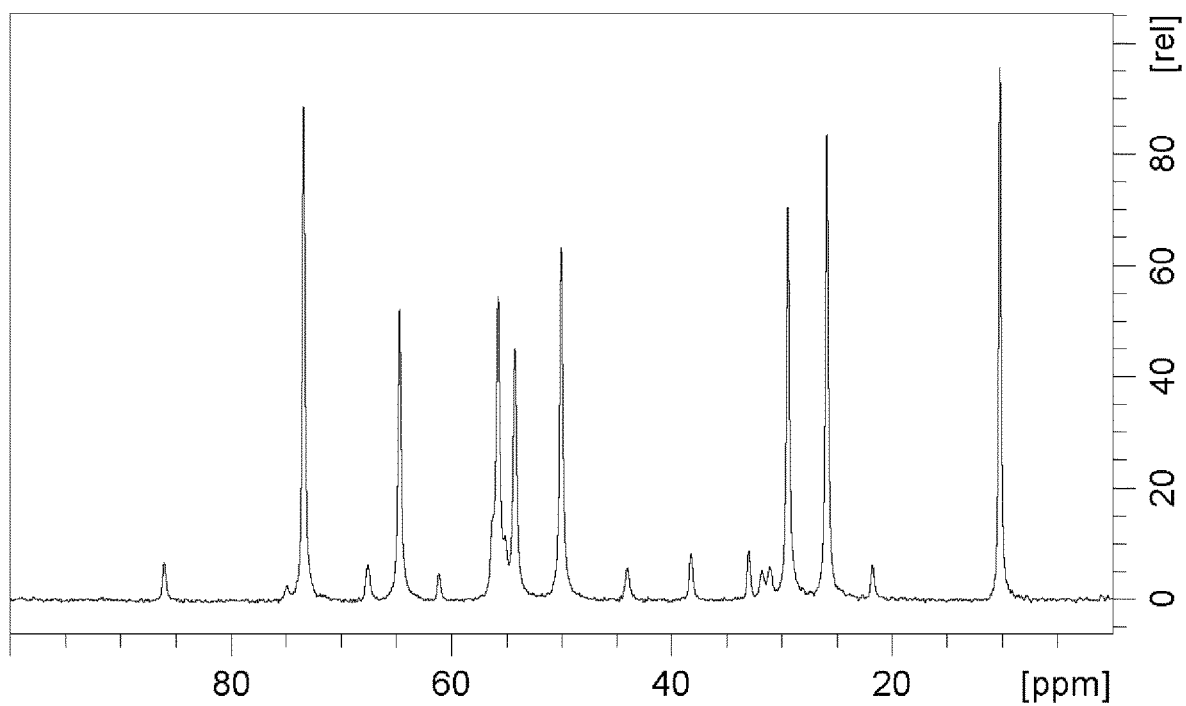

SOLID STATE FORMS OF PEMAFIBRATE

CROSS REFERENCE TO RELATED APPLICATIONS

This application is a National Stage of, and claims priority to and the benefit of, International Patent Application No. PCT/US2018/067012 filed on Dec. 21, 2018, which, in turn, claims the benefit of, and priority to, U.S. Provisional Patent Application No. 62/610,651, filed Dec. 27, 2017, U.S. Provisional Patent Application 62/615,074, filed Jan. 9, 2018, U.S. Provisional Patent Application No. 62/623,227, filed Jan. 29, 2018, U.S. Provisional Patent Application No. 62/631,119, filed Feb. 15, 2018, and U.S. Provisional Patent Application No. 62/645,300, filed Mar. 20, 2018, the entire disclosures of each of which are incorporated by reference herein.

TECHNICAL FIELD

The present disclosure relates to solid state forms of Pemafibrate processes for preparation thereof and pharmaceutical compositions thereof.

BACKGROUND OF THE DISCLOSURE

Pemafibrate has the chemical name (2R)-2-[3-[[1,3-benzoxazol-2-yl-[3-(4-methoxy-phenoxy)-propyl]-amino]-methyl]-phenoxy]-butanoic acid.

Pemafibrate has the following chemical structure:

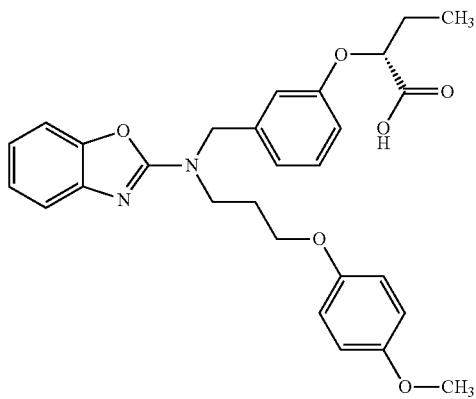 [SMILES: CC[C@@H](Oc1cccc(CN(CCCOc2ccc(OC)cc2)c2nc3ccccc3o2)c1)C(=O)O]

Pemafibrate (PARMODIA®) is a novel, highly selective peroxisome proliferator-activated receptor (PPAR)-α modulator (SPPARM). It acts by binding to PPAR-α and regulating the expression of target genes that modulate lipid metabolism, thereby decreasing plasma triglyceride levels and increasing high-density lipoprotein cholesterol levels. Developed by Kowa Company, Ltd., oral pemafibrate has been approved in Japan for the treatment of hyperlipidaemia (including familial hyperlipidaemia). Further, Pemafibrate is undergoing phase III development in a number of countries for the treatment of dyslipidaemias and is also in phase III development for the treatment of hypertriglyceridaemia.

Pemafibrate is disclosed in U.S. Pat. No. 7,109,226.

Polymorphism, the occurrence of different crystal forms, is a property of some molecules and molecular complexes. A single compound, like Pemafibrate, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for additional solid state forms (including solvated forms or salts) of Pemafibrate.

SUMMARY

The present disclosure relates to solid state forms of Pemafibrate, processes for preparation thereof, and pharmaceutical compositions including this solid state form.

The present disclosure also provides use of the solid state forms of Pemafibrate for preparing other solid state forms of Pemafibrate, Pemafibrate salts and solid state forms of a Pemafibrate salt.

The present disclosure also provides solid state forms of Pemafibrate of the present disclosure for uses in the preparation of other solid state forms of Pemafibrate, Pemafibrate salts and solid state forms of a Pemafibrate salt.

In another embodiment, the present disclosure encompasses the described solid state forms of Pemafibrate for use in the preparation of pharmaceutical compositions and/or formulations, optionally for the treatment and/or prevention of a pathological condition such as hyperlipidemia, arteriosclerosis, diabetes, complications of diabetes, inflammation, and heart diseases.

In another embodiment, the present disclosure encompasses uses of the described solid state forms of Pemafibrate for the preparation of pharmaceutical compositions and/or formulations.

The present disclosure further provides pharmaceutical compositions including one or more solid state forms of Pemafibrate according to the present disclosure.

In yet another embodiment, the present disclosure encompasses pharmaceutical formulations including one or more of the described solid state forms of Pemafibrate and at least one pharmaceutically acceptable excipient.

The present disclosure encompasses processes to prepare said pharmaceutical formulations of Pemafibrate including one or more of the described solid state forms and at least one pharmaceutically acceptable excipient.

The solid state forms defined herein as well as the pharmaceutical compositions or formulations of the solid state forms of Pemafibrate can be used as medicaments, in embodiments for the treatment and/or prevention of a pathological condition such as hyperlipidemia, arteriosclerosis, diabetes, complications of diabetes, inflammation, and heart diseases.

The present disclosure also provides methods of treatment and/or prevention of a pathological condition such as hyperlipidemia, arteriosclerosis, diabetes, complications of diabetes, inflammation, and heart diseases, by administering a therapeutically effective amount of one or more of the solid state forms of Pemafibrate of the present disclosure, or at least one of the herein described pharmaceutical compositions or formulations, to a subject suffering from a pathological condition such as hyperlipidemia, arteriosclerosis, diabetes, complications of diabetes, inflammation, and heart diseases, or otherwise in need of the treatment.

The present disclosure also provides uses of the solid state forms of Pemafibrate of the present disclosure, or at least one of the above pharmaceutical compositions or formulations for the manufacture of medicaments for treating and/or preventing a pathological condition such as hyperlipidemia, arteriosclerosis, diabetes, complications of diabetes, inflammation, and heart diseases.

BRIEF DESCRIPTION OF THE FIGURES

FIG. 1 shows an X-ray powder diffractogram (XRPD) of Form A of Pemafibrate.

FIG. 2 shows an X-ray powder diffractogram (XRPD) of Form B of Pemafibrate.

FIG. 3 shows an X-ray powder diffractogram (XRPD) of Form C of Pemafibrate.

FIG. 4 shows an X-ray powder diffractogram (XRPD) of Form D of Pemafibrate.

FIG. 5 shows an X-ray powder diffractogram (XRPD) of Form B of Pemafibrate.

FIG. 6 shows an X-ray powder diffractogram (XRPD) of amorphous Pemafibrate.

FIG. 7 shows solid state $^{13}$C-NMR spectrum of Form A of Pemafibrate (FIG. 7a: 200-0 ppm; FIG. 7b: 200-100 ppm; FIG. 7c: 100-0 ppm).

FIG. 8 shows solid state $^{13}$C-NMR spectrum of Form B of Pemafibrate (FIG. 8a: 200-0 ppm; FIG. 8b: 200-100 ppm; FIG. 8c: 100-0 ppm).

FIG. 9 shows solid state $^{13}$C-NMR spectrum of Form C of Pemafibrate (FIG. 9a: 200-0 ppm; FIG. 9b: 200-100 ppm; FIG. 9c: 100-0 ppm).

FIG. 10 shows solid state $^{13}$C-NMR spectrum of Form D of Pemafibrate (FIG. 10a: 200-0 ppm; FIG. 10b: 200-100 ppm; FIG. 10c: 100-0 ppm).

DETAILED DESCRIPTION

The present disclosure relates to solid state forms of Pemafibrate, processes for preparation thereof and pharmaceutical compositions including this solid state form. The disclosure also relates to the conversion of the described solid state forms of Pemafibrate to other solid state forms of Pemafibrate, Pemafibrate salts and their solid state forms thereof.

The solid state forms of Pemafibrate according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Pemafibrate referred to herein as being characterized by graphical data "as depicted in" a Figure will thus be understood to include any crystal forms of the Pemafibrate, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or 0% of any other forms of the subject compound as measured, for example, by XRPD. Thus, the solid state form of Pemafibrate described herein as substantially free of any other solid state forms would be understood to contain greater than about 80% (w/w), greater than about 90% (w/w), greater than about 95% (w/w), greater than about 98% (w/w), greater than about 99% (w/w), or 100% of the subject solid state form of Pemafibrate. Accordingly, in some embodiments of the disclosure, the described solid state forms of Pemafibrate may contain from about 1% to about 20% (w/w), from about 5% to about 20% (w/w), or from about 5% to about 10% (w/w) of one or more other solid state forms of the same Pemafibrate.

As used herein, unless stated otherwise, XRPD peaks reported herein are optionally measured using CuK$_\alpha$ radiation, λ=1.54187 Å.

As used herein, the term "isolated" in reference to solid state forms of Pemafibrate of the present disclosure corresponds to solid state form of Pemafibrate that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

The present disclosure includes a solid state form of Pemafibrate designated as Form A. The Form A of Pemafibrate can be characterized by data selected from one or more of the following: an XRPD pattern having peaks at 7.7, 8.2, 11.1, 11.6 and 18.6 degrees 2-theta±0.2 degrees 2-theta; an XRPD pattern as depicted in FIG. 1; and combinations of these data. Crystalline Form A of Pemafibrate may be further characterized by the XRPD pattern having peaks at 7.7, 8.2, 11.1, 11.6 and 18.6 degrees 2-theta±0.2 degrees 2-theta, and also having one, two, three, four or five additional peaks selected from 9.8, 14.1, 16.4, 17.4 and 20.1 degrees 2-theta±0.2 degrees 2-theta.

Crystalline Form A of Pemafibrate may alternatively or additionally be characterized by data selected from one or more of the following: a solid state 13C NMR spectrum with characteristic peaks at 171.2, 158.0, 147.9, 141.1 and 137.7 ppm±0.2 ppm; a solid state $^{13}$C NMR spectrum having the following chemical shift absolute differences from reference peak at 127.8 ppm±1 ppm: 43.4, 30.2, 20.1, 13.3 and 9.9 ppm±0.1 ppm; or by a solid state 13C NMR having the following full peak list: 171.2, 160.3, 158.0, 153.4, 147.9, 141.1, 137.7, 127.8, 121.4, 120.1, 115.3, 111.9, 110.2, 73.2, 63.3, 54.1, 47.8, 39.7, 25.3 and 8.5 ppm±0.2 ppm; or by a solid state $^{13}$C-NMR spectrum substantially as depicted in FIGS. 7a, 7b and 7c; or combinations of these data.

Crystalline Form A of Pemafibrate may be characterized by each of the above characteristics alone/or by all possible combinations, e.g. by XRPD pattern having peaks at 7.7, 8.2, 11.1, 11.6 and 18.6 degrees 2-theta±0.2 degrees 2-theta and an XRPD pattern as depicted in FIG. 1.

The present disclosure includes a solid state form of Pemafibrate designated as Form B. The Form B of Pemafibrate can be characterized by data selected from one or more of the following: an XRPD pattern having peaks at 8.7, 13.1, 17.0, 18.2 and 22.9 degrees 2-theta±0.2 degrees 2-theta; an XRPD pattern as depicted in FIG. 2; an XRPD pattern as depicted in FIG. 5; and combinations of these data. Crystalline Form B of Pemafibrate may be further characterized by the XRPD pattern having peaks at 8.7, 13.1, 17.0, 18.2 and 22.9 degrees 2-theta±0.2 degrees 2-theta, and also having one, two, three, four or five additional peaks selected from 4.4, 7.9, 13.4, 15.2 and 24.2 degrees 2-theta±0.2 degrees 2-theta.

Crystalline Form B of Pemafibrate may alternatively or additionally be characterized by data selected from one or more of the following: a solid state 13C NMR spectrum with characteristic peaks at 173.3, 146.7, 130.8, 119.6 and 115.5 ppm±0.2 ppm; a solid state 13C NMR spectrum having the following chemical shift absolute differences from reference peak at 107.4 ppm±1 ppm: 65.9, 39.3, 23.4, 12.2 and 8.1 ppm±0.1 ppm; or by a solid state 13C NMR having the following full peak list: 173.3, 160.2, 154.4, 153.1, 146.7, 140.3, 139.1, 130.8, 123.3, 121.6, 119.6, 115.5, 112.8, 111.5, 107.4, 74.7, 65.8, 55.1, 52.5, 48.8, 27.2 and 12.6 ppm±0.2 ppm; or by a solid state 13C-NMR spectrum substantially as depicted in FIGS. 8a, 8b and 8c; or combinations of these data.

Crystalline Form B of Pemafibrate may be characterized by each of the above characteristics alone/or by all possible combinations, e.g. by XRPD pattern having peaks at 8.7, 13.1, 17.0, 18.2 and 22.9 degrees 2-theta±0.2 degrees 2-theta and an XRPD pattern as depicted in FIG. 2 or FIG. 5.

The present disclosure further includes a solid state form of Pemafibrate designated as Form C. The Form C of Pemafibrate can be characterized by data selected from one or more of the following: an XRPD pattern having peaks at 5.1, 13.8, 14.7, 16.9 and 17.2 degrees 2-theta±0.2 degrees 2-theta; an XRPD pattern as depicted in FIG. 3; and combinations of these data. Crystalline Form C of Pemafibrate may be further characterized by the XRPD pattern having peaks at 5.1, 13.8, 14.7, 16.9 and 17.2 degrees 2-theta±0.2 degrees 2-theta, and also having one, two, three, four or five additional peaks selected from 8.6, 10.2, 18.3, 19.7 and 21.5 degrees 2-theta±0.2 degrees 2-theta.

Crystalline Form C of Pemafibrate may alternatively or additionally be characterized by data selected from one or more of the following: a solid state 13C NMR spectrum with characteristic peaks at 153.8, 147.9, 139.5, 129.7 and 125.0 ppm±0.2 ppm; a solid state 13C NMR spectrum having the following chemical shift absolute differences from reference peak at 107.3 ppm±1 ppm: 46.5, 40.6, 32.1, 22.4 and 17.6 ppm±0.1 ppm; or by a solid state 13C NMR having the following full peak list: 171.7, 160.7, 156.8, 153.8, 147.9, 142.2, 139.5, 129.7, 125.0, 120.0, 118.0, 116.0, 114.8, 109.6, 107.3, 73.1, 65.7, 54.0, 53.0, 50.5, 28.3, 21.5 and 8.7 ppm±0.2 ppm; or by a solid state 13C-NMR spectrum substantially as depicted in FIGS. 9a, 9b and 9c; or combinations of these data.

Crystalline Form C of Pemafibrate may be characterized by each of the above characteristics alone/or by all possible combinations, e.g. by XRPD pattern having peaks at 5.1, 13.8, 14.7, 16.9 and 17.2 degrees 2-theta±0.2 degrees 2-theta and an XRPD pattern as depicted in FIG. 3.

The present disclosure further includes a solid state form of Pemafibrate designated as Form D. The Form D of Pemafibrate can be characterized by data selected from one or more of the following: an XRPD pattern having peaks at 12.4, 14.2, 16.2, 22.2 and 23.0 degrees 2-theta±0.2 degrees 2-theta; an XRPD pattern as depicted in FIG. 4; and combinations of these data. Crystalline Form D of Pemafibrate may be further characterized by the XRPD pattern having peaks at 12.4, 14.2, 16.2, 22.2 and 23.0 degrees 2-theta±0.2 degrees 2-theta, and also having one, two, three, four or five additional peaks selected from 3.9, 7.9, 8.8, 18.4 and 21.2 degrees 2-theta±0.2 degrees 2-theta.

Crystalline Form D of Pemafibrate may alternatively or additionally be characterized by data selected from one or more of the following: a solid state 13C NMR spectrum with characteristic peaks at 153.3, 146.9, 129.8, 124.0 and 111.8 ppm±0.2 ppm; a solid state 13C NMR spectrum having the following chemical shift absolute differences from reference peak at 107.5 ppm±1 ppm: 45.8, 39.4, 22.3, 16.5 and 4.3 ppm±0.1 ppm; or by a solid state 13C NMR having the following full peak list: 171.8, 160.7, 159.2, 153.3, 146.9, 142.1, 140.9, 129.8, 124.0, 118.8, 117.6, 116.9, 115.4, 111.8, 107.5, 73.3, 64.7, 55.8, 54.2, 50.0, 29.4, 25.9 and 10.2 ppm±0.2 ppm; or by a solid state 13C-NMR spectrum substantially as depicted in FIGS. 10a, 10b and 10c; or combinations of these data.

Crystalline Form D of Pemafibrate may be characterized by each of the above characteristics alone/or by all possible combinations, e.g. by XRPD pattern having peaks at 12.4, 14.2, 16.2, 22.2 and 23.0 degrees 2-theta±0.2 degrees 2-theta and an XRPD pattern as depicted in FIG. 4.

The present disclosure further includes an amorphous form of Pemafibrate. The amorphous form can be characterized by an XRPD pattern as depicted in FIG. 6.

The present disclosure also provides the solid state forms of Pemafibrate of the present disclosure for use in the preparation of other solid state forms of Pemafibrate, Pemafibrate salts and solid state forms thereof.

The present disclosure further encompasses processes for preparing Pemafibrate salts or solid state forms thereof. The process includes preparing the solid state forms of the present disclosure, and converting it to a Pemafibrate salt. The conversion can be done, for example, by a process including reacting the obtained Pemafibrate solid state form with an appropriate acid to obtain the corresponding acid-addition salt In another embodiment, the present disclosure encompasses the above described solid state forms of Pemafibrate for use in the preparation of pharmaceutical compositions and/or formulations, optionally for the treatment and/or prevention of pathological conditions including hyperlipidemia, arteriosclerosis, diabetes, complications of diabetes, inflammation, and heart diseases.

In another embodiment, the present disclosure encompasses the use of the above described solid state forms of Pemafibrate for the preparation of pharmaceutical compositions and/or formulations. The present disclosure also provides the solid state form of Pemafibrate of the present disclosure for use in the preparation of pharmaceutical compositions and/or formulations.

The present disclosure further provides pharmaceutical compositions including one or more of the solid state forms of Pemafibrate according to the present disclosure.

In yet another embodiment, the present disclosure encompasses pharmaceutical formulations including one or more of the above described solid state forms of Pemafibrate and at least one pharmaceutically acceptable excipient.

The present disclosure encompasses processes to prepare said formulations of Pemafibrate including combining one or more of the above solid state forms of Pemafibrate and at least one pharmaceutically acceptable excipient.

The solid state forms of Pemafibrate as defined herein, as well as the pharmaceutical compositions or formulations thereof can be used as medicaments, in embodiments for the treatment and/or prevention of a pathological condition such as hyperlipidemia, arteriosclerosis, diabetes, complications of diabetes, inflammation, and heart diseases.

The present disclosure also provides methods of treating and/or preventing a pathological condition such as hyperlipidemia, arteriosclerosis, diabetes, complications of diabetes, inflammation, and heart diseases, by administering a therapeutically effective amount of one or more of the solid state forms of Pemafibrate in the present disclosure, or at least one of the above pharmaceutical compositions or formulations, to a subject suffering from a pathological condition such as hyperlipidemia, arteriosclerosis, diabetes, complications of diabetes, inflammation, and heart diseases, or otherwise in need of the treatment.

The present disclosure also provides use of the solid state forms of Pemafibrate of the present disclosure, or at least one of the above pharmaceutical compositions or formulations for the manufacture of a medicament for treating and/or preventing a pathological condition such as hyperlipidemia, arteriosclerosis, diabetes, complications of diabetes, inflammation, and heart diseases.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Method:

Powder X-ray Diffraction was performed on an X-Ray powder diffractometer PanAlytical X'pert Pro; CuKα radiation ($\lambda$=1.54187 Å-); X'Celerator detector with active length 2.122 degrees 2-theta; laboratory temperature 25±3° C.; zero background sample holders.

Measurement Parameters:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

Prior to analysis, the samples were gently ground using a mortar and pestle to obtain a fine powder. Optionally, silicon powder can be added in a suitable amount as internal standard in order to calibrate the positions of the diffractions. The ground sample was adjusted into a cavity of the sample holder and the surface of the sample was smoothed using a cover glass.

$^{13}$C Solid State NMR Method:

$^{13}$C CP/MAS NMR spectra were measured at 125 MHz using Bruker Avance III 500 WB/US NMR spectrometer (Karlsruhe, Germany, 2003) at magic angle spinning (MAS) frequency $\omega_r/2\pi$=11 kHz. In all cases finely powdered samples were placed into 4-mm $ZrO_2$ rotors and the standard "cpmas" pulseprogram was used. During acquisition of the data the high-power dipolar decoupling "TPPM" (two-pulse phase-modulated) was applied. The flip-pulse length was 4.8 μs. Applied nutation frequency of $B_1(^1H)$ field was $\omega_1/2\pi$=89.3 kHz. Nutation frequency of $B_1(^{13}C)$ and $B_1(^1H)$ fields during cross-polarization was $\omega_1/2\pi$=62.5 kHz. The number of scans was 2048. Taking into account frictional heating of the samples during fast rotation all NMR experiments were performed at 293 K (precise temperature calibration was performed).

The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

EXAMPLES

Pemafibrate starting material can be prepared according to the synthetic route reported in, e.g., Y. Yamazaki et Al., Tetrahedron 2008, 64, 8155.

Example 1: Preparation of Form A

Pemafibrate (100 mg) was dissolved in acetone (0.4 ml) at room temperature in a vial under air. The vial was capped with aluminum foil with holes and left to evaporate under Nitrogen for 5 days. The solid residue was collected and analyzed by XRD.

Example 2: Preparation of Form A

Pemafibrate (200 mg) was dissolved in MeOH (1 ml) in a vial by heating to reflux with a hair dryer. The resulting solution was left to stand at 4° C. (refrigerator) for 40 hours and the precipitate was collected by filtration.

Example 3: Preparation of Form A

Pemafibrate (200 mg) was dissolved in methyl isopropyl ketone (0.4 ml) in a vial by heating to reflux with a hair dryer. The resulting solution was left to stand at 4° C. for 4 days (refrigerator) and the precipitate was collected by filtration.

Example 4: Preparation of Form A

Pemafibrate (200 mg) was dissolved in ethylene glycol (1 ml) in a vial by heating to reflux with a hair dryer. The resulting solution was left to stand at 4° C. (refrigerator) for 16 hours and the precipitate was collected by filtration.

Example 5: Preparation of Form B

Pemafibrate (100 mg) was dissolved in dimethyl sulfoxide (0.2 ml) at room temperature in a vial under air. The vial was capped with aluminum foil with holes and left at RT to evaporate under nitrogen for 18 days. The residual amount of solution was diluted with water (0.5 ml) and the mixture was stored in a capped vial for 8 days. The solid was collected by filtration and analyzed by XRD.

Example 6: Preparation of Form B

Pemafibrate (500 mg, Form A) was suspended in Acetonitrile (1 ml) in a closed vial. The suspension was heated to 40° C. with thermocouple system and stirred with magnetic agitator for 24 hours. After cooling to 20° C. in around 1 hour, the suspension was filtered over a Buchner funnel with vacuum and the solid was analyzed by XRD.

Example 7: Preparation of Form C

Pemafibrate (5 grams) was added into a 250 ml jacketed glassware reactor equipped with mechanical stirrer and cryostat followed by EtOAc (39 ml) and n-Heptane (78.5 ml). The mixture was heated to reflux observing complete material dissolution. The solution was cooled to 20° C. in 3 hours and then stirred at 20° C. for 1 hour, 15 min. A sample of the suspension was filtered over a Buchner funnel with vacuum and the resulting solid was analyzed by XRD.

Example 8: Preparation of Form D

Pemafibrate (2 grams, Form A) was suspended in Acetonitrile (4 ml) in a closed vial. The suspension was heated at 40° C. with thermocouple system and stirred with magnetic agitator for 24 hours. After cooling to 20° C. in around 1 hour, the suspension was filtered over a Buchner funnel with vacuum and the solid was analyzed by XRD.

Example 9: Preparation of Form D

Pemafibrate (0.5 grams, Form A) was suspended in EtOAc (0.66 ml) and n-Heptane (1.33 ml) in a closed vial. The suspension was heated to 40° C. with thermocouple system and stirred with magnetic agitator for 4 days. After cooling to 20° C. in around 1 hour, the suspension was filtered over a Buchner funnel with vacuum and the solid was analyzed by XRD.

Example 10: Preparation of Form B

Pemafibrate (2 grams, Form A) was suspended in $H_2O$ (40 ml) and dissolved by addition of 1 M NaOH (10 ml) at 20° C. 1 M HCl (10 ml) was added to the solution and the resulting suspension was stirred for around 30 min at 20° C. The product was filtered over a Buchner funnel washing with water (40 ml) and the wet powder (100 mg) was suspended in iPrOH (0.5 ml). The suspension was agitated in a closed vial with orbital shaker for 5 hours at 20° C. and then left to stand for 6 days without agitation at 20° C. The product was filtered over a Buchner funnel and analyzed by XRD.

Example 11: Preparation of Amorphous Pemafibrate

Pemafibrate (1 gram, Form A) was suspended in $H_2O$ (20 ml) and dissolved by addition of 1 M NaOH (5 ml) at 20° C. 1 M HCl (5 ml) was added drop wise to the solution and the resulting suspension was stirred for around 30 min at 20° C. The product was filtered over a Buchner funnel under vacuum and analyzed by XRD.

The invention claimed is:
1. Crystalline Form B of Pemafibrate, which is characterized by data selected from one or more of the following:
   i. an XRPD pattern having peaks at 8.7, 13.1, 17.0, 18.2 and 22.9 degrees 2-theta±0.2 degrees 2-theta;
   ii. an XRPD pattern as depicted in FIG. 2 or 5;
   iii. a solid state $^{13}$C-NMR spectrum with peaks at 173.3, 146.7, 130.8, 119.6 and 115.5 ppm±0.2 ppm;

iv. a solid state $^{13}$C-NMR spectrum having the following chemical shift absolute differences from a peak at 107.4 ppm±1 ppm: 65.9, 39.3, 23.4, 12.2 and 8.1 ppm±0.1 ppm;

v. a solid state $^{13}$C-NMR spectrum substantially as depicted in FIG. 8a; or combinations of (i)-(v).

2. A crystalline form of Pemafibrate according to claim 1, which is characterized by an XRPD pattern having peaks at 8.7, 13.1, 17.0, 18.2 and 22.9 degrees 2-theta±0.2 degrees 2-theta, and also having one, two, three, four or five additional peaks selected from 4.4, 7.9, 13.4, 15.2 and 24.2 degrees 2-theta±0.2 degrees 2-theta.

3. A pharmaceutical formulation comprising a crystalline form according to claim 1, and at least one pharmaceutically acceptable excipient.

4. Crystalline Form B of Pemafibrate, which is characterized by data selected from one or more of the following:

i. an XRPD pattern having peaks at 8.7, 13.1, 17.0, 18.2 and 22.9 degrees 2-theta±0.2 degrees 2-theta;

ii. an XRPD pattern as depicted in FIG. 2 or 5.

5. A crystalline form of Pemafibrate according to claim 4, which is characterized by an XRPD pattern having peaks at 8.7, 13.1, 17.0, 18.2 and 22.9 degrees 2-theta±0.2 degrees 2-theta, and also having one, two, three, four or five additional peaks selected from 4.4, 7.9, 13.4, 15.2 and 24.2 degrees 2-theta±0.2 degrees 2-theta.

* * * * *